US012728142B2

(12) United States Patent
Bonutti et al.

(10) Patent No.: US 12,728,142 B2
(45) Date of Patent: Sep. 8, 2026

(54) SYSTEMS AND METHODS FOR THROMBOSIS PREVENTION

(71) Applicant: P Tech, LLC, Manalapan, FL (US)

(72) Inventors: Peter M. Bonutti, Manalapan, FL (US); Justin E. Beyers, Effingham, IL (US); Tonya M. Bierman, Dieterich, IL (US)

(73) Assignee: P TECH, LLC, Manalapan, FL (US)

( * ) Notice: Subject to any disclaimer, the term of this patent is extended or adjusted under 35 U.S.C. 154(b) by 57 days.

(21) Appl. No.: 18/807,444

(22) Filed: Aug. 16, 2024

(65) Prior Publication Data

US 2025/0090598 A1 Mar. 20, 2025

Related U.S. Application Data

(63) Continuation of application No. 17/661,862, filed on May 3, 2022, now Pat. No. 12,064,456, which is a continuation of application No. 17/091,807, filed on Nov. 6, 2020, now Pat. No. 11,607,431, which is a continuation of application No. 16/210,853, filed on Dec. 5, 2018, now Pat. No. 10,828,339, which is a continuation of application No. 15/155,920, filed on May 16, 2016, now Pat. No. 10,183,044.

(60) Provisional application No. 62/203,708, filed on Aug. 11, 2015, provisional application No. 62/201,891, filed on Aug. 6, 2015, provisional application No. 62/162,361, filed on May 15, 2015.

(51) Int. Cl.

| | |
|---|---|
| ***A61K 36/00*** | (2006.01) |
| ***A61K 31/202*** | (2006.01) |
| ***A61K 31/355*** | (2006.01) |
| ***A61K 31/7034*** | (2006.01) |
| ***A61K 35/60*** | (2006.01) |
| ***A61K 35/644*** | (2015.01) |
| ***A61K 36/45*** | (2006.01) |
| ***A61K 36/76*** | (2006.01) |

(52) U.S. Cl.
CPC ............ *A61K 35/60* (2013.01); *A61K 31/202* (2013.01); *A61K 31/355* (2013.01); *A61K 31/7034* (2013.01); *A61K 35/644* (2013.01); *A61K 36/45* (2013.01); *A61K 36/76* (2013.01)

(58) Field of Classification Search
CPC .................................................... A61K 31/355
See application file for complete search history.

(56) References Cited

U.S. PATENT DOCUMENTS

| | | | | |
|---|---|---|---|---|
| 5,234,695 | A | 8/1993 | Hobbs | |
| 5,720,304 | A * | 2/1998 | Omura | A61P 31/12 128/898 |
| 5,747,533 | A | 5/1998 | Egberg | |
| 6,149,939 | A | 11/2000 | Strumor et al. | |
| 6,930,099 | B2 | 8/2005 | Petrus | |
| 6,994,983 | B2 | 2/2006 | Ens | |
| 7,201,929 | B1 | 4/2007 | Finkelstein | |
| 7,846,914 | B2 | 12/2010 | Petrus | |
| 8,017,657 | B1 | 9/2011 | Petrus | |
| 8,188,146 | B2 | 5/2012 | Peet et al. | |
| 8,293,727 | B2 | 10/2012 | Manku et al. | |
| 8,293,728 | B2 | 10/2012 | Manku et al. | |
| 8,298,554 | B2 | 10/2012 | Manku | |
| 8,314,086 | B2 | 11/2012 | Manku et al. | |
| 8,318,715 | B2 | 11/2012 | Manku et al. | |
| 8,343,753 | B2 | 1/2013 | Chilton et al. | |
| 8,357,677 | B1 | 1/2013 | Manku et al. | |
| 8,367,652 | B2 | 2/2013 | Manku et al. | |
| 8,377,920 | B2 | 2/2013 | Manku et al. | |
| 8,399,446 | B2 | 3/2013 | Manku et al. | |
| 8,415,335 | B2 | 4/2013 | Manku et al. | |
| 8,426,399 | B2 | 4/2013 | Manku et al. | |
| 8,440,650 | B1 | 5/2013 | Manku et al. | |
| 8,445,003 | B2 | 5/2013 | Manku et al. | |
| 8,445,013 | B2 | 5/2013 | Manku et al. | |
| 8,501,225 | B2 | 8/2013 | Manku et al. | |
| 8,518,929 | B2 | 8/2013 | Manku et al. | |
| 8,524,698 | B2 | 9/2013 | Manku et al. | |
| 8,546,372 | B2 | 10/2013 | Manku et al. | |
| 8,551,521 | B2 | 10/2013 | Manku et al. | |
| 8,563,608 | B2 | 10/2013 | Manku et al. | |
| 8,617,593 | B2 | 12/2013 | Manku et al. | |
| 8,617,594 | B2 | 12/2013 | Manku et al. | |
| 8,623,406 | B2 | 1/2014 | Manku et al. | |
| 2003/0069528 | A1 * | 4/2003 | Herz | A61H 9/0007 601/152 |

(Continued)

FOREIGN PATENT DOCUMENTS

| | | | |
|---|---|---|---|
| CN | 101492456 | A | 7/2009 |
| CN | 104144691 | A | 11/2014 |
| DE | 202005007462 | U1 | 7/2005 |
| DE | 202013992760 | U1 | 7/2014 |
| EP | 1714564 | A1 | 10/2006 |
| JP | 2014047194 | A | 3/2014 |
| WO | WO2001031052 | | 5/2001 |
| WO | WO2001084961 | A2 | 11/2001 |

(Continued)

OTHER PUBLICATIONS

Asou et al., A patient with MRSA infection to prosthesis of femoral head diagnosed non-invasively using Bi-Digital O-Ring Test: A clinical case report. Acupuncture and Electro-Therapeutics Research, (2003) vol. 28, No. 1-2, pp. 69-72.

(Continued)

*Primary Examiner* — Qiuwen Mi
(74) *Attorney, Agent, or Firm* — Stinson LLP

(57) ABSTRACT

The disclosure provides a composition for inhibiting thrombosis. The composition includes 5 to 25% by weight of Fish Oil, 15 to 55% by weight of Willow Bark Extract, and 0.2 to 5% by weight of Vitamin E.

20 Claims, 4 Drawing Sheets

(56) References Cited

U.S. PATENT DOCUMENTS

| | | | | |
|---|---|---|---|---|
| 2006/0134233 | A1 | 6/2006 | Stefano et al. | |
| 2006/0217352 | A1 | 9/2006 | Yokoyama | |
| 2007/0193578 | A1 | 8/2007 | Linton et al. | |
| 2008/0260859 | A1 | 10/2008 | Claus-Herz | |
| 2011/0182829 | A1 | 7/2011 | Mandrea | |
| 2013/0030331 | A1 * | 1/2013 | Quisenberry | A61F 7/02 601/18 |
| 2013/0052271 | A1 | 2/2013 | Stemasty | |

FOREIGN PATENT DOCUMENTS

| | | |
|---|---|---|
| WO | WO2009027753 A1 | 3/2009 |
| WO | WO2010083206 | 7/2010 |

OTHER PUBLICATIONS

BDORT, https://en.wikipedia.org/wiki/BDORT, downloaded May 24, 2021, 7 pages.

Chan, The application of “Bi-Digital O-Ring Test” in the diagnosis and treatment of urinary tract infection in symptomatic and asymptomatic patients. Acupuncture & electro-therapeutics research, (1986) vol. 11, No. 3-4, pp. 233-241.

Glynn, “Effects of Random Allocation to Vitamin E Supplementation on the Occurrence of Venous Thromboembolism: Report from the Women’s Health Study,” Circulation, Sep. 25, 2007, 116/13:1497-1503.

David Kritchevsky et al., Nutrition and Disease Update: Heart Disease, 1994. Downloaded May 12, 2015.

Miroslav, Jaw-bone infection examined with bioresonance Bi-Digital O-Ring Test (BDORT) teaches. European Journal of Integrative Medicine, (Sep. 2012) vol. 4, Supp. SUPPL. 1, pp. 120-121 (Year: 2012).

Vitamin E Fact Sheet for Health Professionals, National Institutes of Health, Printed May 5, 2015.

Yoko Sano et al., Blood Coagulation and Fibrinolysis of Rats Fed Fish Oil: Reduced Coagulation Factors Especially Involved in Intrinsic Pathway and Increased Activity of Plasminogen Activator Inhibitor, Bioscience Biotechnology & Biochemistry, 67(10), 2100-2105, 2003.

Sirin et al, Jugular vein thrombosis associated with upper respiratory tract infection. Heart Surgery Forum, (Feb. 2012) vol. 15, Supp. SUPPL. 1, pp. S42. Abstract No. OP-254.

Beth Waldron, et al., Natural supplements, herbs, vitamins and food: Do some prevent blood clots? www.clotconnect.org, May 2013.

Warfarin/Vitamin E (Alpha Tocopherol) >= 800 Units Interactions, Web MD, Drugs & Medications, Downloaded Jan. 17, 2020, 3 pages.

Goeijenbier et al.—Review: Viral Infections and Mechanisms of Thrombosis and Bleeding, Medical Virology vol. 84, Issue 10, pp. 1680-1696, (2012).

Duric et al, Anticoagulant Ativity of Some Artemisia Dracunculus Leaf Extracts, Bosnian Journal of Basic Medical Sciences, May 13, 2015, vol. 15, No. 2, pp. 9-14.

Moreno et al., Effect of Omega-3 polyunsaturated fatty acids on oxidative stress in children and adolescents with autism spectrum disorders. European Neuropsychophamacology, Oct. 2014, vol. 24, Supp. SUPPL. 2, pp. S725, Abstract No. P.7.D.009.

* cited by examiner

SYSTEMS AND METHODS FOR THROMBOSIS PREVENTION

CROSS-REFERENCE TO RELATED APPLICATION

This application is a continuation of U.S. application Ser. No. 17/661,862 filed May 3, 2022, which is a continuation of U.S. application Ser. No. 17/091,807, filed Nov. 6, 2020, issued as U.S. Pat. No. 11,607,431, which is a continuation of U.S. application Ser. No. 16/210,853, filed Feb. 5, 2018, issued U.S. Pat. No. 10,828,339, which is a continuation of U.S. application Ser. No. 15/155,920, filed May 16, 2016, issued U.S. Pat. No. 10,183,044, and claims the benefit from U.S. Provisional Application No. 62/162,361 filed May 15, 2015, U.S. Provisional Application No. 62/201,891 filed Aug. 6, 2015, and U.S. Provisional Application No. 62/203,708 filed Aug. 11, 2015, the entire contents of which are incorporated herein by reference.

BACKGROUND

The field of the disclosure relates generally to thrombosis prevention, and more specifically, to methods and systems for prevention of deep vein thrombosis perfusion, or general clot prevention.

Generally, thrombosis or thrombotic events are instances when a blood clot is formed inside a blood vessel. The clot can obstruct the flow of blood to tissue and result in tissue damage, swelling, and pain. There has been suggestion that anti-platelet agents can be effective to limit or decrease the risks of arterial thrombosis in and around the heart. However, there is a need for compositions of prophylaxis or prevention of thrombosis in the venous system of a body, especially in the legs, calves, and/or upper extremities.

BRIEF DESCRIPTION

In one aspect, a composition for preventing thrombosis is provided. The composition includes an anti-platelet agent configured to affect platelet aggregation within blood of a user and an essential fatty acid that is configured to affect intrinsic pathways of the blood.

The features, functions, and advantages that have been discussed can be achieved independently in various embodiments or may be combined in yet other embodiments, further details of which can be seen with reference to the following description and drawings.

DETAILED DESCRIPTION

The systems and methods described herein are directed to compositions and/or combinations of compositions for prevention and/or prophylaxis of thrombotic events. More specifically, the systems and methods described herein are directed to compositions and/or combinations of compositions for prevention and/or prophylaxis of thrombotic events in the venous system of a body. The compositions and/or combinations of compositions of the present disclosure are obtained by combining at least two of: willow bark, aspirin, vitamin E, and an essential fatty acid. Specifically, the present disclosure relates to the daily administration of at least two of willow bark, aspirin, vitamin E, and an essential fatty acid in separate preparations, or in preparations that contain combinations of the ingredients, or preferably, in a single lozenge.

As used here, the terms "blood clot," "thrombus," "thrombotic event," and/or "thrombosis" are defined as platelets and/or fibrin in blood adhering to form a mass that can reduce blood flow through a vessel. An "embolus" or "embolism" is at least a portion of a thrombus moving from an initial location to a position through the bloodstream. As used herein, the terms "artery", "arteries", "arterial system", or "arterial side" refers to a vessel or vessels that carry blood high in oxygen content away from the heart to the farthest reaches of the body. Since blood in arteries is usually full of oxygen, hemoglobin in the red blood cells is oxygenated resulting in blood looking bright red. Likewise, as used herein, the terms "vein", "veins", "capillary", "capillaries", "venous system", or "venous side" refers to vessels that carry blood low in oxygen content from the body back to the heart. The deoxygenated form of hemoglobin (deoxyhemoglobin) in venous blood makes it appear dark.

Daily doses of the compositions or treatments defined herein are aimed at reducing, preventing, and/or prophylaxis treatment of thrombotic events in the venous system and organs of the body and are comprised of at least two of: (1) willow bark; (2) aspirin; (3) vitamin E; and (4) an essential fatty acid. Throughout the description of the compositions or treatments described herein, the term "dosage" will refer to a daily dosage—i.e., the total dosage administered in a single day. A dosage, therefore, may comprise one or more dosage forms and one or more administrations of such dosage forms in a single day.

Figure 1:
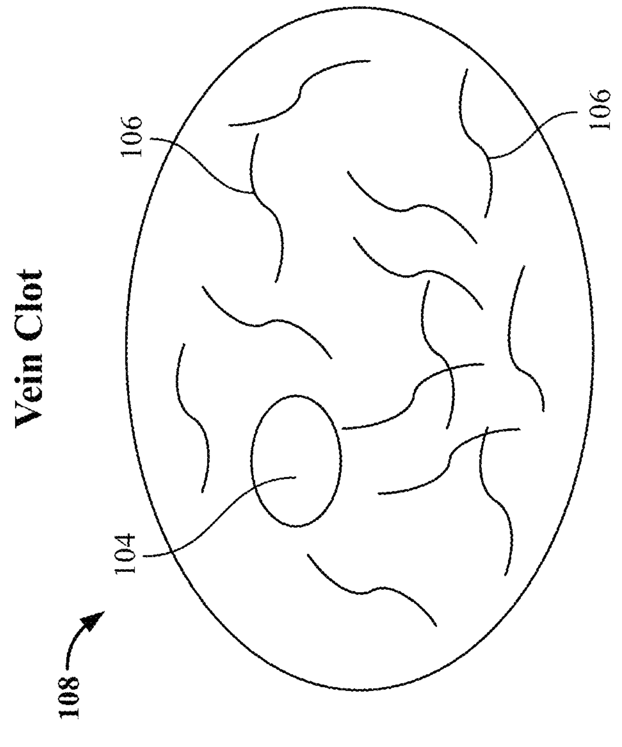
FIG. 1 is an illustration of an exemplary thrombosis occurring in the arterial system and the venous system.
Figure 1:
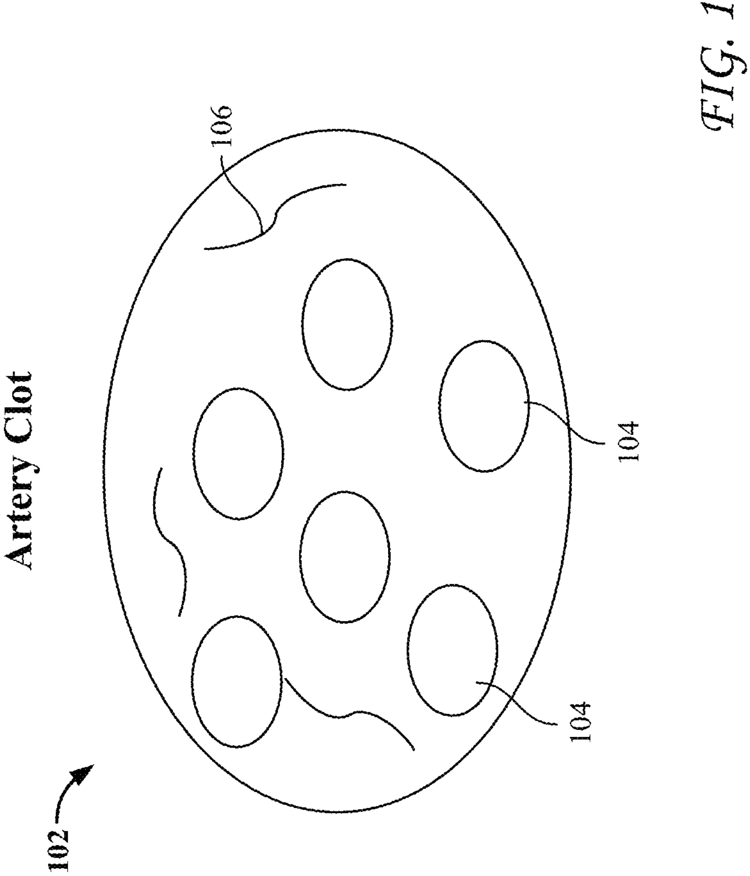

Generally, thrombosis can occur both in the arterial (high flow) side and the venous (low flow) side. As shown in FIG. 1, thrombosis in the arterial system 102 is formed mostly from platelet 104 aggregation whereas thrombosis in the venous system 108 occur mostly of fibrin 106. As such, issues on the venous side often relate to more fibrin 106 in the clotting factors rather than platelet 104 aggregation. Therefore, known techniques to prevent and/or eliminate thrombosis from the arterial system may not be effective in prevention in the venous system as the clot formation in each system differs.

Blood clots affecting the venous system often occur in the lower leg veins, tibialis anterior, posterior tibialis, popliteal, or further up in femoral or iliac veins and are known as a deep vein thrombosis (DVT). It has been hypothesized that a portion of a DVT can break off and travel to the area in and around the heart causing a pulmonary embolism often resulting in mortality of a patient. Additionally, DVT can also cause chronic venous insufficiency damage to the valves within the venous system. Chronic venous insufficiency causes significant lower extremity swelling and pain. This is also further complicated by certain diseases such as diabetes where there is decreased skin healing enabling skin stretch to the point of causing infection. Skin can breakdown and develop ulcerations ultimately resulting in infections and even amputations due to chronic venous insufficiency which may be sequelae of DVT. Risks of this are substantial. As such, DVT prevention is critical for individuals who are static. Some non-limited examples of individuals that are static are those lying in bed, patients with limited mobility postoperatively due to a cast, patients that have undergone total hip and/or total knee arthroplasty, as well as sedentary individuals.

Current treatment and modalities of patient care require mandated DVT Prophylaxis (i.e. treatments to prevent DVT from forming) when patients undergo surgical procedures or are admitted to hospitals. Known treatments can include pulsatile stockings, aspirin, and/or factor Xa inhibitors. Medications used in prophylaxis can include Xarelto, Arixtra, Lovenox, and Coumadin. Many of these medications have significant and severe complication risks including severe risks of bleeding and death. The risks of bleeding can result in issues such as severe pain, hematoma formation, especially in the postoperative period, abdominal bleeds, or issues of severe bleeding within the brain (e.g. stroke). Numerous lawsuits have been initiated due to excessively strong anticoagulation treatment using the aforementioned medications.

Xarelto, Eliquis, Arixtra, Lovenox, Heparin, and Coumadin are agents that are commonly used in DVT prophylaxis but require a prescription, blood test, and close monitoring of the Prothrombin time (PT) and international normalized ratio (INR) to ensure the patient is not over anticoagulated or under anticoagulated. In addition to regular blood tests, the agents above may also require daily injections and can be difficult to reverse. Even with such extensive monitoring, a question of efficacy and the true prevention of DVT exists. It is hypothesized that the benefits associated with Coumadin and other pharmaceutical prophylaxis lend themselves to treating an existing DVT rather than preventing formation of a DVT. In some DVT prophylaxis applications, Aspirin is utilized because of the effects on platelet aggregation. However, many clinicians do not recommend aspirin as an effective agent to prevent DVT as it only affects platelets and platelet adhesion and not the intrinsic clotting pathways which is critical in venous thrombosis as opposed to arterial thrombosis which is primarily platelet. It is important to note that additional agents are used to affect Factor X inhibitors and the intrinsic clotting pathway system but are extremely expensive and have severe complications which can be life threatening. As such, the costs and risks are significant with prescription medication.

Optimal treatments to prevent thrombosis, and more specifically DVT, proposed herein include not only modalities that would affect platelet function but would also affect the intrinsic pathway. In the exemplary embodiment, treatments to prevent thrombosis includes an anti-platelet agent such as Aspirin or willow bark or those described in more detail below. Aspirin is an acetylsalicylic acid. Aspirin in doses of 81 mg to up to 325 mg twice a day is a simple agent that can be given over-the-counter and has anti-platelet function but does not affect the intrinsic pathway or Vitamin K mediated anticoagulation. In some embodiments, willow bark (active agent Salicin) is utilized as an anti-platelet that also is effective for pain relieve including headache, muscle pain, menstrual cramps, rheumatoid arthritis (RA), osteoarthritis, gout, and ankylosing spondylitis. In one embodiment, willow bark doses of 81 mg to up to 325 mg twice a day can be used as an herbal substitution for aspirin that would affect anti-platelet function. As such, it should be noted that the treatments described herein having an anti-platelet agent (e.g. aspirin or willow bark) can substitute aspirin for willow bark and vice versa. As used herein, the term "willow bark" refers to any agent having the active ingredient Salicin. In some embodiments, willow bark refers to a medicine created from one or more willow trees including white willow or European willow, black willow or pussy willow, crack willow, purple willow, and others.

Essential fatty acids (EFAs) are naturally occurring unsaturated fatty acids with a chain length of 18, 20, or 22 carbon atoms. The body cannot synthesize these EFAs, hence, dietary intake of EFAs is required. Two fatty acids which fall within the family of EFAs are eicosapantaenoic acid (EPA) and docosahexaenoic acid (DHA), both of which are commonly found in fish oils. Another fatty acid which falls into the family of EFAs are Alpha linolenic acid (ALA) which is typically derived from vegetable oils including, but not limited to, canola, soybean, flax seed, and walnut. ALA can be converted to Omega 3 fatty acids, but this conversion to the body is modest and controversial. Epidemiological observations indicate that EFAs reduce platelet aggregation and serum triglycerides which may reduce the risk of myocardial infarction, hypertension, atherosclerosis, and certain types of cancer. Specifically, it has been shown that EPA and DHA derived from fish oils play important structural roles in membranes of most cells, and influence the fluidity of the cell membranes as expressed by decreased whole-blood viscosity and increased erythrocyte flexibility and deformability. In addition, EFAs such as EPA and DHA are known precursors of eicosanoids-a class of compounds which includes prostanoids such as prostaglandins and thromboxanes, leukotrienes, and hydroxy fatty acids. Eicosanoids are known are known to affect platelet aggregation, permeability and tone of the blood vessel walls, blood pressure, and inflammatory immune reactions.

Fish oil dietary supplementation is known to have other beneficial health effects. EPA and DHA are beneficial for Hypertriglyceridemia and may have an effect on cardiac disease with many other associated factors such as effects on clinical depression, anxiety, cancer, hypertension, Crohn's disease, and macular degeneration. Glycogen storage disease is an inherited disorder, and is often complicated by severe hyperlipoproteinemia and hypercholesterolemia, which increase the risk of premature atherosclerosis and cardiovascular diseases. It has been reported that patients suffering from glycogen storage disease that received 10 grams of fish oil for 3 months experienced a significant decrease in levels of triglycerides in the blood serum (−49%) and cholesterol levels in the blood serum (−23%), and a reduction in LDL levels in the blood serum (−40%), and a significant increase in HDL levels in the blood serum (+30%). In some instances, some fish oils have been known to decay or oxidize over time (e.g. 2 days). In one embodiment, krill oil is utilized as a source of EPA and/or DHA because it includes natural antioxidants that slow or retard the oxidation and/or decay of the effectiveness of the fish oil.

Fish oil also has anti-inflammatory effect in doses of 500 mg to 1.8 grams. Typical capsules come in 400-500 milligrams where typical are 280 mg of DHA and 120 mg of EPA. In some instances, fish oil is taken up to 6 grams per day. Some studies suggest EPA/DHA, and fish oil can affect both the intrinsic and extrinsic pathway. It is thought that EFAs may reduce levels of Factor VIII and Factor IX in the intrinsic clotting cascade pathway. This would decrease the intrinsic clotting pathway to help DVT prophylaxis. This combined with anti-platelet agents (e.g. aspirin and/or willow bark in 81 mg to 325 mg) is very efficacious for DVT prophylaxis. In some embodiments, a powdered form of EFA is used in the formulations described herein. In one embodiment, the powered form of EFA is derived from plants (e.g. algae, seaweed) rather than animals (e.g. fish).

Vitamin E (Y-Tocopherol) is a fat-soluble antioxidant that protects body tissue from damage caused by free radicals.

Free radicals can harm cells, tissues, and organs as they are believed to play a role in certain conditions related to aging. It is an alpha- and gamma-tocopherol. Minimum daily requirement is 15 mg. Vitamin E supplements only provide approximately 100 IU in a tablet. Many adults need over 11.3%. Adults take over 400 IU daily. Vitamin E is useful in keeping the immune system strong against viruses and bacteria. Vitamin E is also important in the formation of red blood cells and helps the body use vitamin K. It also helps widen blood vessels preventing clot formation. Vitamin E also protects polyethylene unsaturated lipids from peroxidation. To date, little or no evaluation on the efficacy of EFAs for treatment of prevention of DVT either as an isolated entity or in combination with anti-platelet agents or Vitamin E has been done. In some embodiments, Vitamin E is provided to additionally slow or retard the oxidation and/or decay of the effectiveness of the EFA. In some embodiments, Vitamin E provides nausea relief associated with intake of Sacilin and/or EFAs. Multifactorially, Vitamin E and Salicin affect platelet aggregation while Fish oil and Omega 3, specifically EPA, affects clotting cascade, in a multimodal treatment.

In an exemplary embodiment, to obtain the benefits of anti-clotting and avoid the expense and complications inherent with current pharmaceuticals, a treatment is created using a combination of at least two of willow bark, vitamin E, and an essential fatty acid or at least two of aspirin, vitamin E, and an essential fatty acid. In such an embodiment, the treatment provides prevention of thrombosis and/or DVT in a non-prescription (e.g. over the counter) form. In one embodiment, the treatment includes an anti-platelet agent such as aspirin or willow bark in doses of 81 mg a day up to 325 mg twice a day combined with an EFA (e.g. fish oil) in doses of as little as 250 mg a day to up as much as 3 grams or more per day. Doses of 300-500 mg of EPA and DHA are minimal daily recommendations and doses greater than 3 grams per day have been known to increase the risks of complications including bleeding, however, doses between are beneficial. In some embodiments, vitamin E is added to the treatment from a dose of 1-200 mg a day up to 1 gram per day. In some embodiments, a buffering agent (e.g calcium carbonate) is utilized to minimize any stomach irritation that can be caused by the aspirin and/or willow bark. Such a treatment would be very cost effective as well as treatment effective approach for prevention of DVT which is a combination not just postoperatively but also in patients who are sedentary or have episodes of reduced activity. Long term higher doses may actually be used to treat venous thrombosis in this combination protocol. For example, a combination protocol can include fish oil and for example vitamin E if the patient has allergies to aspirin or aspirin based compound or has significant GI risks.

The treatment described herein can be combined to be manufactured as a single tablet, capsule, powder, water soluble powder, gummy, intravenous injectable (iv), or quick melt tablet. Additionally, the treatment can be taken as a combination dosage which would be taken with two or more separate tablets, capsules, or gummies. In some embodiments, the treatment and/or composition described herein is suspended in a fluid medium suitable for parenteral administration into a mammal. In some embodiments, the treatment and/or composition described herein is manufactured as a food, including but not limited to, brownies, cookies, hard or soft candies, yogurts, and chocolates. Many older patients have trouble swallowing large capsules of vitamins and medications (e.g. fish oil, vitamin E, etc) and as such, in one embodiment, the formulations described herein are combined into a powder which are manufactured into a quick melt tablet that enables a user to chew and or melt in the mouth and/or body. In some embodiments, flavorings are added to promote compliance with a suggested regime. Flavorings can be derived from vegetation (e.g. fruits, vegetables, and herbs) or manufactured using known synthetic techniques. Flavorings can be anything that changes the natural taste of the formulations described herein including, but not limited to, strawberry, raspberry, chocolate, coffee, mocha, vanilla, lemon, and citrus. In one embodiment, dark chocolate derivatives are added to provide anti-platelet effects and to buffer flavor of the formulations described herein. In some embodiments, additives are provided to decrease gastrointestinal irritation such as burping, gas, and nausea.

In a combination dosage, a buffered aspirin or willow bark (e.g. 81-325 mg) is combined with an EFA (e.g. ~240 mg/1,000 fish oil) and Vitamin E (e.g. 15-40 mg) to affect both platelet function and intrinsic pathways without requiring blood monitoring or a prescription in a cost effective manner. In addition to affecting platelet function and intrinsic pathways, the treatment described herein provides an anti-inflammatory effect as well as other beneficial effects such as brain function and reducing cardiovascular disease for general health, and heart health perfusion flow through small vessels, cognitive brain function.

In the exemplary embodiment, the treatment includes a combination of an anti-platelet approach, which could be Aspirin, willow bark, or other anti-platelet agent and EFAs (e.g. fish oil including 240 mg EPA and 360 mg DHP) to decrease platelet aggregation, but also are known to affect the intrinsic and extrinsic blood coagulation profiles. These agents used in combination, (i.e. anti-platelet approach with a medication that decreases coagulation pathways in the body) is effective. In addition, the treatment described herein provides specific benefits such as 1) having anti-inflammatory effect, 2) having antioxidant effect, 3) improving mild depression and anxiety, 4) aiding in muscle strength and energy, and 5) operating synergistically to enhance certain cardiovascular functions. These medications are safe as they are known to be over-the-counter, but when used in combination either daily or twice a day may substantially decrease the rate of venous thrombosis. 1) Treatment for day of immobilization, for length of immobilization. 2) Start day before or day of travel for one week. 3) Start day of use of testosterone, birth control pills, estrogen. Additionally, the formulations provided herein provide safety to a patient as the affects can be reversed with Vitamin K or the injection of additional plasma.

Willow bark, EFAs, and vitamin E are often given as a nutraceutical or nutritional supplements, but they have not been used in combination to help treat DVT, prevent DVT, or limit the risks of clotting without requiring complex prescription medications. Additionally, the treatment described herein may be offered in combination for other health benefits with or without other thrombosis prevention technology (e.g. TED hose).

In some non-limiting examples, the treatment to prevent thrombosis could take the following combinations: 1) EFA and aspirin; 2) EFA and vitamin E; 3) EFA alone; 4) EFA, aspirin, calcium carbonate and/or other antacid; 5) EFA, vitamin E, willow bark; 6) Combination of 2 separate pills the first having EFA and vitamin E and the second having aspirin and an antacid; 7) EPA 8) EPA with an antioxident. In an exemplary embodiment, a formulation including Salicin in the range of 81-325 mg, EPA in the range 240 mg-1 gram, and Vitamin E in the range of 15-40 mg is provided.

In one embodiment, thrombosis prevention is achieved by providing EPA alone. In such an embodiment, pure EPA used as anticoagulant to prevent DVT. The EPA can be dosed in the range of 240 mg to 1000 mg. In one embodiment, the pure EPA is provided in 240 mg, however, any dosage of pure EPA can be provided including, but not limited to, 480, 720, and 1000 mg. It should be noted that the pure EPA may be derived from animals (e.g. fish, krill, etc.) or from plants (e.g. seaweed, kelp, algae). In some embodiments, DHA and ALA are provided alone to a patient, to enable the body to convert each into EPA.

In one embodiment, anti-inflammation components can be added to aid in the body's recovery post-surgery or trauma. Some non-limiting examples of anti-inflammatory components include cumin, frankincense & myrrh, olive oil, cannabis, hemp, and arnica. Moreover, additional anti-platelet agents could be used to supplement and/or replace the use of aspirin and/or willow bark. Such anti-platelet agents include, but are not limited to, garlic, ginger, ginko biloba, grape seed, cannabis, kava, papain, dong quai, aloe, aloe juice, lumbrokinase, evening prime rose oil, nattokinase, magnesium, coenzyme Q-10, glucosamine, lyopene/tomatoes, L-arginine, taurine, feverfew, selenium, onion, resveratrol, B-group vitamins, and danshen. In some embodiments, intrinsic pathways are affected with the use of EFAs, vitamin E, and/or papain. In one embodiment, a combination of Vitamin D and Vitamin C are added the formulations described herein to provide additional vasodilation of vessels.

In one embodiment, an extract of a salicylate containing spice, food, and/or beverage is added to the formulations described herein to provide additional antithrombotic effects to a user. Some salicylate containing spices and/or herbs include, but are not limited to, Cinnamon, Tumeric, Curry powder, Oregano, Peppermint, Cayenne, Ginger, Paprika, Thyme, Dill, Garam masala. Some salicylate containing foods and/or beverages include, but are not limited to, fruits such as blueberries, cranberries, grapes, cherries, strawberries, nectarine, tangerines, and oranges, honey, vinegar, black tea, green tea, pineapple juice, red wine, and white wine.

Coumarin is a natural product, similar to Coumadin that could be used to also affect internal clotting cascade. In some embodiments, Coumarin is provided in the formulations described herein. Some Coumarin derivatives include, but are not limited to, Alfalfa, Angelica root, Aniseed, Arnica, Artemesia, Asa foetica (asafetida), Bael fruit, Bilberry, Bishop's weed, Bogbean, Buchu, Capsicum, Cassia cinnamon, Celery seed, Chamomile, Cloudberry, Chicory, Danshen (salvia miltiorrhiza), Dandelion, Dong quai (Danggui, Angelica sinensis), Fenugreek, Horse chestnut, Horseradish, Lavender, Licorice root, Lovage root, Meadowsweet, Melilot, Nettle, Parsley, Passion flower, Prickly ash, Quassia, Red clover, Rue, Sweet clover, Sweet woodruff, Tonka beans (high levels of coumarin), Wild carrot, Wild lettuce, the essential oils of cassia oil, cinnamon bark oil, and lavender oil, and green tea. In some embodiments, Coumadin could be used as an adjunct to Coumarin.

These combination doses could be varied to the patient's needs. Dosages could be in one single pill (e.g. combining an anti-platelet agent, an EFA, and vitamin E in one quick melt tablet). Alternatively, multiple pills could be used. For example, aspirin and antacid could be in one pill and EFA and vitamin E could be combined in a separate pill. If the patient has risks for aspirin, history of ulcers, or aspirin allergy, one could substitute with willow bark, other anti-platelet agents, and/or provide a combination of just vitamin E and an EFA once a day or twice a day.

The treatment described herein could be provided short term (i.e. starting preoperatively or pre-hospitalization for one day up to one week) and continued postoperatively or post-hospitalization for two weeks or for as long as three months after surgery, injury, or while the patient is wearing cast, immobilizer, or limited ambulator. The treatment is a safe effective over-the-counter agent of combination therapy to reduce the risks of DVT and risks of complications from surgery or injury. The combinations of Vitamin E, EFAs, and/or anti-platelet agent can decrease the risks of bleeding. This has been identified during surgical procedures as well as in postoperative evaluations with blood loss.

The best effect for prophylaxis would be not only treating intrinsic pathway but also anti-platelet agents such as aspirin or potentially Plavix. This could be modulated from as little as 500 mg per day to as much as 6 grams per day of fish oil with aspirin or willowbark going from 81 mg to 325 mg b.i.d. (2× a day) and vitamin E ranging from 15 mg per day to up to 1,000 mg a day. Dosage may be stratified by weight, size and risk factors including obesity, prior DVT, prior history of pulmonary embolism, diabetes, venous insufficiency, prior history of cancer, or active cancer. These could also be given in homeopathic doses, lower doses, or to prevent the risks of DVT in patients who have cancer.

In addition to surgical patients, another key risk category for DVT and pulmonary emboli are women who are taking birth control pills or participating in an estrogen regime. These patients would benefit from the risks of DVT, thrombosis, or even stroke using the treatments described herein. Additionally, males who are taking steroid supplements such as testosterone supplements would see benefit from a regime of the treatments described herein. In some embodiments, the treatments can be given to patients who have active cancer as it would decrease the risks of DVT and/or thrombosis which is elevated in these patients. In some instances, the treatments could be used as long term maintenance treatment in patients who have prior incidence of DVT to prevent recurrence rather than using pharmaceuticals (e.g. Coumadin or Warfarin) which requires regular monitoring of PT levels by intravenous blood draw or through more risky agents such as Xarelto, Arixtra, Lovenox, etc. As described above, pharmaceuticals can be expensive and require prescriptions as well as having significant risks for complications including bleeding, stroke, etc.

Another classic area of thrombotic risk is for patients who currently have stents and require anti-thrombolytic therapy for stents. Anti-thrombolytic therapy is expensive and has significant side effects. The treatments described herein would be a better form and safer form of long term treatment for patients who have had prior history of stent placement to prevent thrombosis. The combination approach could be used for intrinsic and extrinsic pathways of coagulation including Factor VIII, Factor IX, and Factor X. This could be accomplished with the treatment described herein that includes a combination of at least two of EFAs, vitamin E, as well as an anti-platelet (e.g. aspirin or willow bark). For example, it would be extremely effective in this combination to prevent thrombosis or reclotting of patients who have had stents. Doses can be varied depending on the size of patient, weight, and risk factors.

Additionally, diabetics are known to have thrombotic risk as issues with small vessel disease (e.g. arteries, capillaries, or venules) often occur in this group. In small vessel disease, the arterial supply diminishes and one can get ulceration, neurologic disease, such as diabetic neuropathy where the peripheral nerve loses perfusion in small vessels and nerves stop functioning, sensory numb, weak, then motor later, and/or small vessel disease of the eyes (retinopathy). A diminished arterial supply in combination with small vessel constriction and the potential of small vessel thrombi micro-emboli, causes secondary skin tissue and/or microtrauma to internal organs. Diabetics benefit from the use of the formulations described herein as the formulations provide vasodilatation as well as vascular flow improvement and embolization prevention. In one embodiment, the formulations described herein could be manufactured into a topical application. In such an embodiment, the formulations described herein can be combined with a vasodilator (e.g. nitro paste or beta-blocker) to further dilate these small blood vessels and improve flow which would decrease the risks for damage toxicity, organ failure (e.g. kidney or skin), or assist with the prevention or formation of diabetic ulcers. Vitamin E dilates, topical ultrasound or nitroglycerin can dilate and improve flow in small vessels.

It has been surprisingly found that that the combination of an anti-platelet agent and EFAs function synergistically to decrease the risk of venous thrombosis and can be used as prophylaxis for deep vein thrombosis postoperatively and/or post immobilization. The treatments can be secondarily used to prevent blood clotting in the arterial flow such as after stent placement, open heart surgery, as well as after vascular procedure which may be of benefit. In addition, because of the known nutraceutical effect, the treatment provides benefits beyond clotting prevention as previously identified. It has been surprisingly found that the EFAs used in combination with other agents enhance fibrinolysis in users. The enhancement of fibrinolysis is of value in preventing thrombosis (e.g. DVT) because of the increased amount of fibrin in the venous system as opposed to the arterial system.

It has been unexpectedly found the combination of the formulations synergistically increase anti-inflammatory effects as well as improves postoperative cardiac health, triglyceride level, cardiac blood flow, and decreases the risks for depression and anxiety and help with analgesia and muscle strength. It has been unexpectedly found that the formulations described herein have a beneficial effect on the prostaglandins.

It has also been unexpectedly found that the formulations described herein treat the internal clotting cascade of the venous system. Unlike the arterial or high flow systems of a body, the venous systems in the body often have more fibrin in the clotting factors rather than platelet aggregation in the arterial systems.

It was surprisingly found in compositions that contain certain portions of EFAs and an anti-platelet agent, when observed relative to that provided by individual components, that there was decreased blood aggregation as the coagulation times were prolonged and a decreased rate and risks of deep vein thrombosis postoperatively and/or post immobilization. The sum of the combination is substantially more effective than the sum of the individual effect not only in the anti-thrombotic effects (i.e. preventing blood clots in the deep veins and lower extremities after immobilization or surgery) but it also has numerous beneficial additive effects that can enhance patients that are immobilized and have recently had surgery and/or injury. It is certainly far superior than prescription medications such as Coumadin, which requires very close blood monitoring and blood testing on a regular basis. Additionally, agents such as Arixtra or Xarelto have severe side effects including risks of mortality due to excessive bleeding, strokes, etc. Lovenox also has severe complications and bleeding risks. These agents are specifically instructed not to use with Aspirin or anti-platelet medications especially for prophylaxis of deep vein thrombosis as they would markedly increase the rate of severe inhibition of either Factor X or the intrinsic pathways and/or thrombin production. In addition, agents such as Xarelto cannot be reversed whereas a combination of fish oil and/or Aspirin and/or Vitamin E with or without other anti-platelet agents can easily be reversed with the addition of platelets (e.g. Vitamin K use of blood plasma). None of the other agents (i.e. Arixtra, Xarelto, and Lovenox) are easily reversed and if a complication occurs, these can be catastrophic. Whereas the combination of an anti-platelet agent, EFA, and/or Vitamin E is safe, physiologic, and has numerous advantages in addition to their ability to prophylax against thrombosis, and more specifically, DVT.

The synergistic effects are observed when active compounds are applied jointly, however, they can also be observed when the active compounds are used independently or sequentially. For example, the EFA can be applied at different times than the anti-platelet agent. EFAs can be given once a day, anti-platelet agent once a day, but they can be alternating schedules or they can be given twice a day treatment for anti-platelet agent or up to three times a day for EFA although the half-life of the medication with anti-platelet effect may only require once a day dosage. In some embodiments, 325 mg of an anti-platelet agent twice a day with 1 gram of EFA once or twice a day in combination can be effective as combination therapy as well as have numerous beneficial effects both with positive cardiovascular effects such as decreasing triglyceride levels as well as improving energy, muscle strength, etc. In some embodiments, these are split and taken at different times or different combinations with different dosages. EFA can be increased up to 6 grams a day and anti-platelet agent up to 325 mg b.i.d (2× a day). The EFA can be given all as one dose or timed over the course of the day and up to 6 separate doses.

The overall treatment time for prophylaxis of deep vein thrombosis depends on the reason for treatment. For example, if the patient has a cast on, one would use it for the treatment time the cast is on. If one has had total knee replacement, postoperatively, one would consider starting the medications several days preoperative. For example, a patient would begin the preoperatively. In some embodiments, before surgery, an EFA is used singularly, alternatively, and EFA is used in conjunction with at least one of an anti-platelet agent and/or vitamin E. Once the surgery is performed, the treatment is maintained for a period of little as 2 weeks to as long as 3 months. An anti-platelet agent may be required only after surgery because many anesthesia agents such as epidural or spinal cannot be applied due to anti-platelet effects of aspirin and/or willow bark. Once the surgery is completed and anesthesia is completed, an anti-platelet agent and/or additional components can be provided. In some embodiments, treatment includes increasing the doses postoperatively from 1 gram a day to possibly 1-2 grams a day, EFA and 325 mg of anti-platelet agent up to once or twice a day and/or vitamin E 15 mg up to 100 mg a day if needed depending on the risk factors. If risk factors are increased, for example if patient does have prior deep vein thrombosis, prior cardiac event, patient is significantly overweight with BMI over 35, or history of carcinoma/cancer, the treatment levels can be increased as well as dose and frequency. If the patient has risks for bleeding (i.e. easy bleeding during surgery or has certain forms of hemophilia) lower doses, modified doses, or limited doses are possible with EFAs alone at 500 mg to 1 gram a day for prophylaxis in these patients. In some embodiments, treatment for a surgical procedure is started with willow bark and fish oil 1-2 days before the procedure and is used in conjunction with a regional block during surgery.

The present invention may provide a kit for treating the patient. For example, preoperatively for treatment prior to total knee replacement, one would have 5 days preoperatively with only taking an EFA +/− willow bark, and/or possibly vitamin E. In one embodiment the preoperative dose is 1 gram a day. Alternatively, the preoperative dose can be any dosage that provides benefit to the patient based on patient specific factors. Once the surgery is performed, the patient would take EPA 1 gram to 2 grams a day, an anti-platelet 325 mg b.i.d., and/or Vitamin E 15 mg to 40 mg a day. These would be provided daily. In some embodiments, at the 2 week level, the dosage is tapered to the anti-platelet once a day and EFA once a day with discontinuing vitamin E. In some embodiments, at a point between 4 weeks or 12 weeks, all of components of treatment would be discontinued.

In some embodiments, if someone is treated with cast or where one is immobilized on best rest, the patient would be treated with higher dose of the anti-platelet and EFA during the entire time one is completely bedridden. In such an embodiment, when one regains limited ambulation, a dosage of 1 gram a day of EFA and 325 mg a day of an anti-platelet is given until one is fully ambulatory and active again. The treatment courses and kits may be shorter for those who may have arthroscopic procedures in which one may start 3-4 days preoperatively and only continue for 1-2 weeks postoperatively. For example, for spinal surgery depending on the degree of immobilization, one may start an anti-platelet the first postoperative day, start an EFA 2-3 days preoperatively and then anti-platelet and EFA combination postoperatively but waiting 24 hours after to start this so there would not be any bleeding in/around the spine.

The treatments may be presented in a dispenser device such as a kit which may have the appropriate agents each day or twice a day dosage which could be packaged as a kit. They could be separate pills or a single pill. There could be one pill that is salt base with calcium carbonate that would buffer. For example an enteric-coated anti-platelet (e.g. aspirin) packaged with EFA and/or vitamin E tablet. These could be packaged in appropriate dosages each day. There may be one package for knee arthroplasty or hip arthroplasty, another package for shoulder surgery, another packet for casting or bedrest. Different packaging can be combined based on length, time, and dosage required. These could be tapered before injury, surgery, or trauma and then increased once immobilization or decreased activity occurs and then taper down as activity increases. The kit may be packaged sterilely in single pack with foil opened up on a daily basis and may be monitor as a kit over a 30 day treatment or 20 day treatment based on the treatment protocol required for risk factors of deep vein thrombosis.

In some embodiments, the treatment for prevention of thrombosis is done orally and/or topically. In one embodiment, the entire treatment is delivered topically and locally to a site. In an alternative embodiment, a patient would ingest a combination of components systemically and apply one or more components locally to a site through a topical application. For example, a patient might ingest a pill containing aspirin, fish oil, and/or vitamin E. The patient would then apply a salve having at list an anti-inflammation component to help reduce swelling and/or pain. In one embodiment, the skin of the patient (e.g. pores) is dilated to allow penetration of the salve. Dilation can occur using techniques including, but not limited to, rasping of the skin and applying salt to the skin. In some embodiments, the topical application is driven into the skin for greater depth of penetration and assisting in entering cell walls more efficiently with the use of topical ultrasound. In some embodiments, methods and systems used to deliver the topical application are as those described in U.S. patents application Ser. Nos. 11/549,994, 11/867,679, 13/789,658 to Bonutti et al., all of which are incorporated by reference herein. In one embodiment, a pH altering agent is utilized within the formulations described herein or separately to change the local pH to enable greater depth of penetration.

In some embodiments, the treatments described herein are used in conjunction with additional thrombosis prevention techniques. For example, in addition to ingesting one or more of the treatments described herein, an external energy unit (e.g. ultrasound, electrical stimulation, laser) provides energy internally and/or externally to a patient to prevent or breakup thrombosis. Additionally, an appliance may be positioned on or about a body part to provide thrombosis prevention. In some embodiments, the appliance includes, but is not limited to an elastic sleeve, a compressive stocking, TED hose, tourniquet, pulsatile stocking, or other graduated compressive device. In some embodiments, an external energy unit is integrated into an appliance. In such an embodiment, the appliance may applying compressive pressure to the body. In some embodiments, the compressive pressure is obtained through with intermittent pulses of compressed air, which sequentially inflate multiple chambers in the stocking, resulting in a wave-like milking action, which forcibly assists blood flow through the veins and results in greatly increased peak blood flow velocity. The external energy units are integrated to the appliance and may be used in conjunction with the wave-like milking action of the appliance to breakup or prevent any type of thrombin or clot formation. As the intermittent pulses of compressed air sequentially inflate multiple chambers in the pulsatile stocking, a controller unit activates energy units, directing energy (e.g. ultrasound) into the body. The controller unit may selectively activate the external energy units in a continuous sequence or in a pulsating sequence producing a pulsed energy. The combination of the wave-like milking action of the appliance and directed energy from the external energy units work in unison to prevent the formation of and break-up clotting or plaque formations. In some embodiments, delivery of energy to the body is achieved in a manner similar to that disclosed in U.S. Pat. No. 8,750,983, all of which is herein incorporated by reference.

Figure 2:
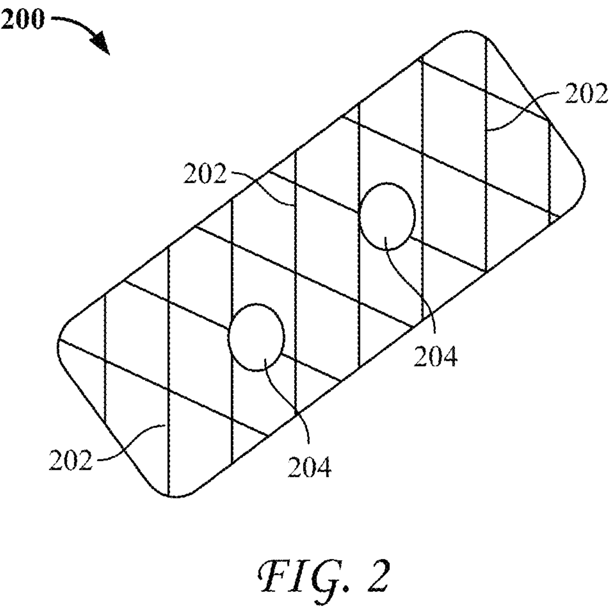
FIG. 2 is an illustration of a thrombosis prevention device.

Currently, some known external thrombosis prevention devices (e.g. balloon devices and compressive stockings) can be bulky and require external pumps to operate. In an exemplary embodiment, as shown in FIG. 2, a thrombosis prevention device 200 is used including the use of shape memory alloys or shape memory polymer fabrics 202 to increase the flow within vessels to prevent and/or eliminate thrombosis. In such an embodiment, the shape memory alloys 202 are controlled by heat, and in the case of conductive alloys 202, such as Nitinol, electrical current is passed through the alloy to heat and change the shaped of the alloy. It is contemplated that other non-conductive polymers 202 could be used with an external heat source or other known method for actuating the polymers 202. The use of shape alloys, fibers, or polymers 202 enable a fabric to conform to a wearer to provide a compressive and/or constrictive force on the skin of a user. In the exemplary embodiment, active fibers are woven into a fabric to form an elastic stocking or wrap stocking.

The use of shape alloys, fibers, or polymers 202 provide a manner in which a conformable fabric or stocking can provide the desired mechanical actions necessary to reduce the risk of thrombotic events without the need of bladders. Such an embodiment also provides a uniform fit ensuring accurate mechanical action being performed on the skin of a user. Additionally, the portability of fabrics and stockings would be substantially reduced as the need of an air compressor is eliminated. To this, while the compression forces in balloon devices are limited and/or fixed based on the air pressure provided to the bladders, the use of shape alloys, fibers, or polymers ensure that compression devices (e.g. socks, stockings, wraps) can be monitored and adjusted ensuring safety of the user. In one embodiment, as shown in FIG. 2, a monitoring component 204 is integrated into the device. In the exemplary embodiment, the monitoring component is a sensor configured to monitor at least the compressive force exerted on the skin of a user. The sensor can be any sensor that measures forces including, but not limited to, force sensors, load cells, air bladders, and/or devices that use electrical current for actuation, and have an electrical property such as impedance that changes with the amount of resistance or opposing force.

Figure 3:
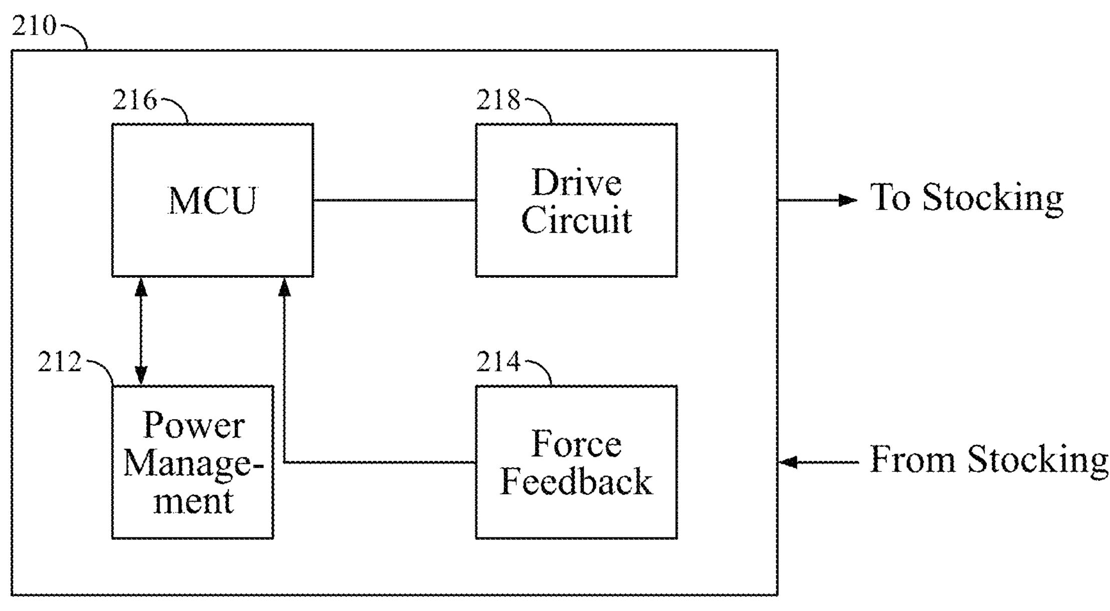
FIG. 3 is a block diagram of an exemplary control unit for use with the thrombosis prevention device of FIG. 2.

As shown in FIG. 3, device 200 is communicatively coupled to a control unit 210 having a control circuit 212 that communicates with the sensors 204 shown in FIG. 2. In one embodiment, sensors 204 communicate with control unit 210 through a wired connection. Alternatively, in some embodiments, the sensors 204 communicate with control unit 210 wirelessly through known wireless protocols. In operation, a force feedback component 214 receives a signal sent from sensors 204 and conditions the signal for processing by a micro controller unit (MCU) 216. The MCU 216 sends a signal a drive circuit 218 for actuation of at least one of the shape alloys, fibers, or polymers based on the feedback received from the sensors 204.

Figure 4:
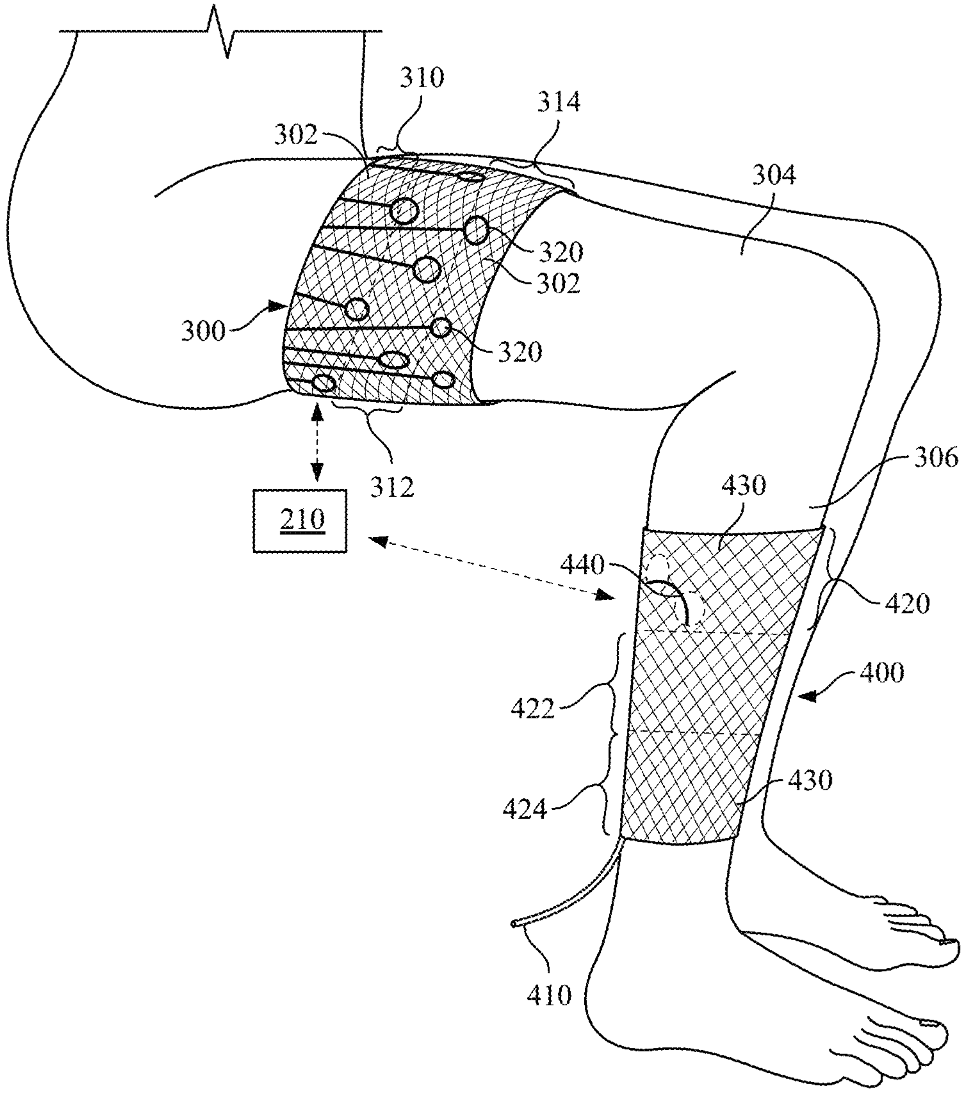
FIG. 4 is a perspective view of exemplary thrombosis prevention devices.

FIG. 4 is a perspective view of exemplary thrombosis prevention devices 300 and 400 for use in prevention of clots. In some embodiments, devices 300 and 400 include the components and features of device 200 and control unit 210. For example, devices 300 and 400 are shown being communicatively coupled to control unit 210. In the exemplary embodiment, devices 300 and 400 and unit 210 are electrically coupled. Alternatively, devices 300 and 400 and unit 210 can be coupled in a wireless configuration to send and receive information over wireless transmission links including, but not limited to Bluetooth (RF), WAN, LAN, and cellular. In such an embodiment, devices 300 and 400 and unit 210 would each include a communication interface coupled to a processor to enable communication interface to send and transmit data. The communication interface may include, for example, a wired network adapter, a wireless network adapter, and/or a mobile telecommunications adapter.

In the exemplary embodiment, device 300 is a sleeve or wrap configured to securely conform around a patient's limb (e.g. thigh, lower leg, or abdomen). Device 300 is shown to be secured around a leg 304 of a patient and includes a plurality of shape memory fibers 302, such as fibers 202 shown in FIG. 2. In the exemplary embodiment, device 300 includes a plurality of zones 310, 312, and 314. Zones 310, 312, and 314 enable fibers 302 to provide a compressive force on the patients limb and/or skin. The compressive forces provided are sufficient to compress veins, capillaries, and/or arteries to restrict and/or move blood. In some embodiments, device 300 includes a plurality of energy transmission devices 320 for providing energy transdermally to the tissue. Devices 320 can provide any energy to the tissue including, but not limited to, radio frequency (RF), magnetic, electro magnetic (EM), acoustic, microwave, thermal, vibratory, radiation, or extracorporeal shockwave (ESW) energies.

Referring to the lower leg (e.g. calf) 306 of a patient, device 400 is an air compression wrap or garment. Device 400 is coupled to a bladder inflation device (not shown) such as an air compressor, via a hose 410. Device 400 includes a plurality of bladders or chambers 420, 422, and 424 that are supplied fluid media by hose 410 from the inflation device. The fluid media provided by hose 410 is supplied to the chambers 420, 422, and 424 such that a compressive force is applied to the contact points of the user. In some embodiments, device 400 includes shape memory fibers 430, such as fibers 202 shown in FIG. 2. The fibers 430 provide a compressive force in addition to that supplied by chambers 420, 422, and 424. The compressive forces provided by fibers 430 and/or chambers 420, 422, and 424 are sufficient to compress veins, capillaries, and/or arteries to restrict and/or move blood. In some embodiments, device 400 includes a plurality of energy transmission devices 440 for providing energy transdermally to the tissue. Devices 440 can provide any energy to the tissue including, but not limited to, radio frequency (RF), magnetic, electro magnetic (EM), acoustic, microwave, thermal, vibratory, radiation, or extracorporeal shockwave (ESW) energies.

In operation, unit 210 provides instructions for compression of devices 300 and 400. More specifically, unit 210 provides instructions for fibers 302 and/or 430 to change shape or provide a compressive force. The devices 300 and 400 are configured to provide sequential compression, through zones 310, 312, and 314 and/or chambers 420, 422, and 424 to provide a wave-like milking action, which forcibly assists blood flow through the veins and results in greatly increased peak blood flow velocity. While devices 300 and 400 are shown having three zones or chambers, it should be noted that any number of zones or chambers could be used including, but not limited to, one, two, four, six, ten, and twelve.

In some embodiments, devices 300 and/or 400 provides heating and/or cooling to the tissue captured under the device. In one embodiment, a chamber coupled in flow communication with device 300 and/or 400 provides media and/or air flow to the tissue that is warm/hot or cold/cool relative to the tissue. In such an embodiment, media or temperature controlled air travels over the fabric to the tissue. In some embodiments, the fibers 302 and/or 430 are electrically charged to generate heat which is transmitted to the tissue.

Figure 5:
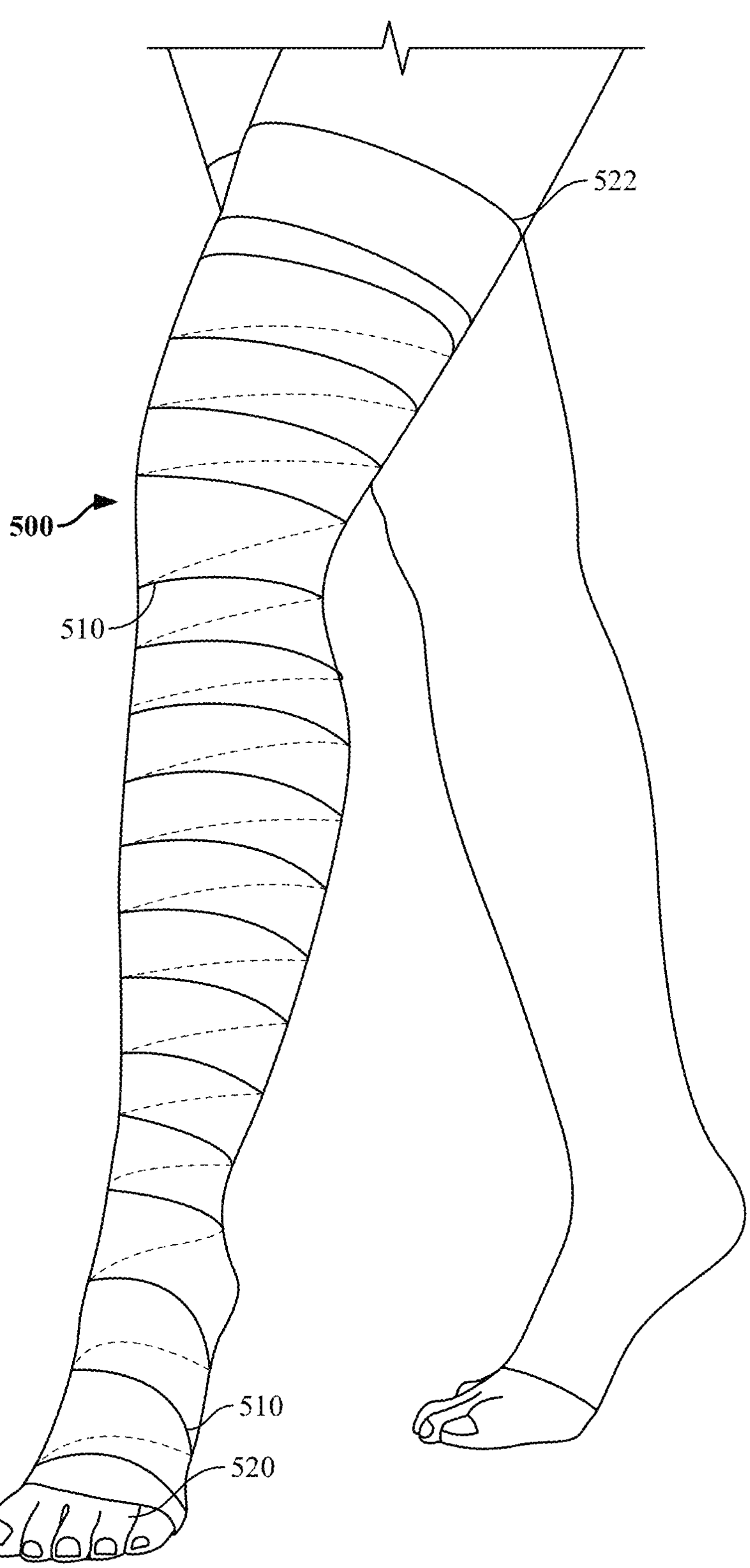
FIG. 5 is an alternative thrombosis prevention device.

FIG. 5 is an alternative compression device 500 for use in prevention of clots. Device 500 can be configured to include all of the components of devices 200, 300, and/or 400. In the exemplary embodiment, device 500 includes a plurality of fibers 510 that extend from a first aperture 520 to a second aperture 522. In one embodiment, the fibers 510 are oriented in a spiral configuration that enables control unit 210 to transmit signals forcing the fibers to excite and/or move in a spiral motion in a direction to or from the first aperture 520. Although device 500 is shown having one spiral pattern, multiple spiral patterns (e.g. helix) could be provided to enable an efficient wave-like milking action, which forcibly assists blood flow through the veins and results in greatly increased peak blood flow velocity. Additionally, fibers 510 can be oriented in such a manner to provide any pastern that would facilitate moving blood through the veins, capillaries, and/or arteries.

Although devices 300, 400, and 500 are shown as being coupled to the leg of a patient or user, it should be noted that the devices described herein could be used and configured to conform to any body part and any body type including, but not limited to, the chest, abdomen, and arms. It should also be noted that devices 300, 400, and 500 can be manufactured as a sleeve that has to be manually pulled on and off for placement. In such an embodiment, a device holder that is configured to stretch the device can be used such that a user can place a portion of a body part (e.g. foot or hand) in the holder and the device can be rolled into position on the user. Alternatively, devices 300, 400, and 500 can be manufactured as a wrap having a securement mechanism that would enable a user to quickly release the device from the body. The securement mechanism can be any component that would enable the device to remain on the user through the compression including, but not limited to, a hook and loop configuration, magnetic attraction, clasps, zipper, and a friction fit. In one embodiment, devices 300, 400, and 500 are fabricated with a permanently compressible fiber such that, after securing on a user by manually positioning or securing a securement mechanism, the device must be destroyed (e.g. cut) to remove.

It should be noted that the devices described herein can be used in imaging (e.g. CT, MRI, X-ray, ultrasound, nuclear, mammography) of soft tissue. When multiple images of soft tissue are taken the resulting image can often be difficult if not impossible to read due to movement of the soft tissue. The devices described herein would enable portions of a body's soft tissue (e.g. breast) to be compressed and inhibit movement to enable more accurate imaging of the tissue. As such, the devices described herein provide a manner to increase the effectiveness of imaging soft tissue and abnormalities seen therein (e.g. tumors).

The embodiments described herein enable prevention of thrombosis and more specifically of DVT. The embodiments described herein provide safe and cost effective prevention of thrombosis in addition to providing beneficial secondary effects including, but not limiting to, antioxidant effects, anti-inflammatory effects, cognitive effects, and cardio protective effects. As compared to at least some known thrombosis prevention systems, the systems and methods described herein do not require a prescription, do not require blood test monitoring, do not have irreversible risks of bleeding, and do not generally have severe potential complications associated with the treatments.

The synergistic effects are clearly stronger than the usual effects of individual items. The synergistic effects present additional anti-inflammatory, antioxidant, cardiac beneficial effects as well as decreased risks of deep vein thrombosis. Prophylaxis for deep vein thrombosis could also have many cardiovascular benefit effects with limited risk factors. The effects are reversible if there are increased risks of bleeding.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose various embodiments, which include the best mode, to enable any person skilled in the art to practice those embodiments, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method of treating thrombosis in a subject, the method comprising:

administering to the subject a pharmacologic agent composition to reduce clotting, wherein the pharmacologic agent composition comprises at least two bioactive agents selected from the group consisting of an antiplatelet agent, an essential fatty acid, and an antioxidant;

securing an appliance to a body portion of the subject; and transmitting energy into the body portion of the subject from at least one energy unit coupled to the appliance and positioned on the body portion of the subject, wherein the energy transmitted is configured to break up thrombosis in the body portion of the subject.

2. The method of claim 1, wherein the antiplatelet agent comprises at least one of willow bark extract, or aspirin.

3. The method of claim 1, wherein the antioxidant comprises Vitamin E.

4. The method of claim 1, further comprising administering a coumarin component comprising coumarin or a coumarin derivative.

5. The method of claim 1, wherein the pharmacologic agent composition further comprises an anticoagulant.

6. The method of claim 1, wherein the pharmacologic agent composition is in the form of a tablet, a capsule, a food, a powder, a gummy, or quick melt tablet.

7. The method of claim 1, wherein the appliance comprises at least one of an elastic sleeve, a compressive stocking, a thrombo-embolic deterrent (TED) hose, a tourniquet, or a pulsatile stocking.

8. The method of claim 1, further comprising applying a compressive force to the body portion of the subject to which the appliance is secured.

9. The method of claim 1, wherein the transmitted energy is at least one of acoustic energy, or ultrasonic energy.

10. The method of claim 1, wherein the essential fatty acid (EFA) comprises at least one of eicosapantaenoic acid (EPA), or docosahexaenoic acid (DHA).

11. A method of preventing thrombosis in a subject, the method comprising:

administering to the subject a pharmacologic agent composition to reduce clotting, wherein the pharmacologic agent composition comprises at least two bioactive agents selected from the group consisting of an antiplatelet agent, an essential fatty acid, and an antioxidant;

securing an appliance to a body portion of the subject; and transmitting a fluid from an inflation device into a plurality of bladders or chambers in the appliance to apply a compressive force to the body portion of the subject contacted by the appliance, wherein the appliance comprises at least one of a compression wrap or garment configured to couple to the inflation device.

12. The method of claim 11, wherein the antiplatelet agent comprises at least one of willow bark extract, or aspirin.

13. The method of claim 11, wherein the antioxidant comprises Vitamin E.

14. The method of claim 11, further comprising administering a coumarin component comprising coumarin or a coumarin derivative.

15. The method of claim 11, wherein the pharmacologic agent composition further comprises an anticoagulant.

16. The method of claim 11, wherein the pharmacologic agent composition is in the form of a tablet, a capsule, a food, a powder, a gummy, a quick melt tablet, or an injectable.

17. The method of claim 11, wherein the applied compressive force is configured to, in the body portion of the subject, at least one of i) prevent thrombin formation, ii) prevent clot formation, iii) break-up thrombin formation, or iv) increase vascular flow.

18. The method of claim 11, further comprising controlling the plurality of bladders or chambers to inflate in succession to provide sequential compression against the body portion of the subject to at least one of increase blood flow in the body portion of the subject, or reduce swelling in the body portion of the subject.

19. The method of claim 11, further comprising at least one of heating the body portion of the subject contacted by the appliance, or cooling the body portion of the subject contacted by the appliance.

20. The method of claim 11, wherein the essential fatty acid (EFA) comprises at least one of eicosapantaenoic acid (EPA), or docosahexaenoic acid (DHA).

* * * * *